United States Patent [19]

Carpenter et al.

[11] Patent Number: 5,160,313
[45] Date of Patent: Nov. 3, 1992

[54] PROCESS FOR PREPARING TISSUE FOR TRANSPLANTATION

[75] Inventors: John F. Carpenter; Kelvin G. M. Brockbank, both of Marietta, Ga.

[73] Assignee: Cryolife, Inc., Marietta, Ga.

[21] Appl. No.: 699,873

[22] Filed: May 14, 1991

[51] Int. Cl.$^5$ ............................................... A61F 2/04
[52] U.S. Cl. ........................................ 600/36; 62/62; 623/901; 128/DIG. 27
[58] Field of Search ............. 62/62, 65; 128/DIG. 27; 600/36; 623/11, 901

[56] References Cited

U.S. PATENT DOCUMENTS

| | | | |
|---|---|---|---|
| 3,303,662 | 2/1967 | Moline | 62/62 |
| 4,423,600 | 1/1984 | McKenna | 62/62 |
| 4,890,457 | 1/1990 | McNally et al. | 62/65 |

FOREIGN PATENT DOCUMENTS 8901286 2/1989 PCT Int'l Appl. .

OTHER PUBLICATIONS

Hempling, *Mass Transfer of Liquids Across Biological Barriers*, in The Biophysics of Organ Cryopreservation pp. 51-63 (D. Pegg & A. Karow eds. 1987).
Cryolife Cardiovascular, Inc., *Clinical Program Allograft (Homograft) Heart Valves*, pp. 16-20 (1989).
Louagie, et al., *Viability of Long-Term Cryopreserved Human Saphenous Veins*, J. Cardiovasc. Surg. 31:92-100 (1990).
Lange and Hopkins, *Allograft Valve Banking: Techniques and Technology* in Cardiac Reconstructions with Allograft Valves, pp. 55-60 (R. Hopkins ed. 1989).
Bank, et al., *Cryogenic Preservation of Isolated Rat Islets of Langerhans: Effect of Cooling and Warming Rates*, Diabetologia 16:195-199 (1979).
Clifton and Hanna, *Corneal Cryopreservation and the Fate of Corneal Cells in Penetrating Keratoplasty*, Amer. J. of Ophthalmology 78:239-250 (1974).
Fielding and Pegg, *Homograft Skin Banking—Current Practices and Future Trends*, Aust. N.Z.J. Surg. 58:153-156 (1988).
Jensen, et al., *Intraocular Grafts of Fresh and Freeze-Stored Rat Hippocampal Tissue: A Comparison of Survivability and Histological and Connective Organization*, J. Comparative Neurology 227:558-568 (1984).
Karp, *The Use of Free-Hand Unstented Aortic Valve Allografts for Replacement of the Aortic Valve*, J. Cardiac Surg. 1:23-32 (1986).
Hullett, et al., *Successful Long-Term Cryopreservation and Transplantation of Human Fetal Pancreas*, Diabetes 38:448-453 (1989).
Kay and Ross, *Fifteen Years' Experience with the Aortic Homograft: The Conduit of Choice for Right Ventricular Outflow Tract Reconstruction*, Annals of Thoracic Surg. 40:360-364 (1985).
Kirklin, et al., *Intermediate-term Fate of Cryopreserved Allograft and Xenograft Valved Conduits*, Annals of Thoracic Surg. 44:598-606 (1987).
Langdon, et al., *Reconstruction of Structure and Cell Function in Human Skin Grafts Derived from Cryopreserved Allogeneic Dermis and Autologous Cultured Keratinocytes*, J. Investigative Dermatology 91:478-485 (1988).
Pegg, *The Nature of Cryobiological Problems*, in Low-Temperature Biotechnology 3-21 (J. McGrath & K. Diller, eds. 1988).
Rajotte, et al., *Transplantation of Cryopreserved and Fresh Rat Islets and Canine Pancreatic Fragments: Comparison of Cryopreservation Protocols*, Cryobiology 20:169-184 (1983).
Redmond, et al., *Cryopreservation, Culture, and Transplantation of Human Fetal Mesencephalic Tissue into Monkeys*, Science 242:768-771 (1988).
Rothmund and Wagner, *Assessment of Parathyroid Graft Function After Autotransplantation of Fresh and Cryopreserved Tissue*, World J. Surg. 8:527-533 (1984).
Sabiston, et al., *Transplantation of the Rabbit Medial Collateral Ligament. II. Biomechanical Evaluation of Frozen/Thawed Allografts*, J. Orthopaedic Res. 8:46-56 (1988).
Sandler and Anderson, *The Significance of Culture for Successful Cryopreservation of Isolated Pancreatic Islets of Langerhans*, Cryobiology 21:503-510 (1984).
Schachar, *Cryopreservation of Articular Cartilage for Transplantation*, Sapporo Med. J. 56:157-161 (1987).
Sørensen, et al., *Intracephalic Transplants of Freeze-Stored Rat Hippocampal Tissue*, J. Comparative Neurology 252:468-482 (1986).
Taylor and Benton, *Interaction of Cooling Rate, Warming Rate and extent of Permeation of Cryoprotectant in Determining Survival of Isolated Rat Islets of Langerhans During Cryopreservation*, Diabetes 36:59-65 (1987).
Toledo-Pereyra, et al., *Cryopreservation of Islets of Langerhans*, Cryobiology 18:483-488 (1981).
Vasir, et al., *Normalization of Hyperglycemia in Diabetic Rats by Intraportal Transplantation of Cryopreserved Islets From Four Donors*, Diabetes 38:185-188 (1989).
Wagner, et al., *The Effect of Cryopreservation on Hormone Secretion in vitro and Morphology of Human Parathyroid Tissue*, Surg. 99:257-264 (1986).
Whittingham and Leibo, *Survival of Mouse Embryos Frozen to $-196°$ and $-269°$ C.*, Science 178:411-414 (Oct. 27, 1972).
Adam, et al., *The Effect of Liquid Nitrogen Submersion on Cryopreserved Human Heart Valves*, Cryobiology 27:605-614 (1990).

Primary Examiner—Paul Prebilic
Attorney, Agent, or Firm—Kenyon & Kenyon

[57] ABSTRACT

A method is disclosed for preparing a transplantable tissue which has been cryopreserved with an intracellular cryoprotectant and then thawed. After thawing, the tissue is treated with a diluent (or eluent) solution to reduce the level of cryoprotectant in the cells to a substantially non-toxic level. This is conducted using a single dilution step. Cryoprotectants which are removable in this manner include dimethylsulfoxide, glycerol, propanediol and other compounds which penetrate the cells.

The dilution step does not require end point titration and can be conducted over a time period greater than about 5 minutes.

22 Claims, No Drawings

PROCESS FOR PREPARING TISSUE FOR TRANSPLANTATION

BACKGROUND

The invention described herein relates to a process for preparing transplantable tissue which has been cryopreserved and stored at cryopreservation temperatures. Success of certain tissue transplants relies in large measure upon the level of cell and tissue viability, which is defined as the ability of a cell or tissue to maintain itself and interact in a normal manner with its environment. With the steady increase in frequency of transplant surgery, techniques for tissue preservation, storage, thawing and cryoprotectant elution have become increasingly important for preserving tissue viability.

The invention described herein relates to a process for treating transplantable tissue after cryopreservation and thawing so as to elute (or dilute) the intracellular cryoprotectant which is frequently used. Intracellular cryoprotectants pose particular difficulties during transplant preparation due to temperature dependent chemical cytotoxicity. In addition, osmotic stress can be created due to hyperosmotic levels of solutes in the thawed cells.

Dilution techniques used to elute the cryoprotectant from cryopreserved tissues after thawing have traditionally used a multi-step procedure, seeking to minimize both the chemical cytotoxicity and the cellular osmotic shock, which in combination result in cell stress and potentially in cell death. Stepwise elution of the intracellular cryoprotectant minimizes the net diffusion of water into the cells, and permits the intracellular cryoprotectant to diffuse out. The multi-step approach tends to be time consuming and requires particular attention to details such as elution times, temperatures, etc. Since this relatively complex elution process is typically conducted in the operating room during a surgical procedure, it is advantageous to use the simplest, safest thawing and elution process with the least number of steps, thus permitting the operating room personnel to focus on the surgical procedure at hand.

The object of the present invention is to provide a one-step intracellular cryoprotectant elution method which reduces the cryoprotectant concentration within tissues to substantially non-toxic levels (to the constituent cells of the tissue) at which the tissue can be safely transplanted.

Another objective of the present invention is to provide a dilution process which requires a minimum number of steps.

Another objective of the present invention is to provide a process which requires no end point titration or determination.

Another objective of the present invention is to speed and simplify the elution process for the preparation of cryopreserved tissue in order to facilitate transplant surgery. These and other objectives will be apparent to those of ordinary skill in the art from the teachings herein.

SUMMARY OF THE INVENTION

An improved process for treating transplantable tissue is disclosed wherein tissue, which has been cryopreserved with an intracellular cryoprotectant and thawed, is treated in a one step elution procedure which comprises eluting the intracellular cryoprotectant with an eluent solution to a substantially non-toxic intracellular concentration prior to transplant.

DETAILED DESCRIPTION

As used herein, the term "transplantable tissue" refers to cellular tissue wherein the cells are accompanied by (or held within) an extracellular matrix. Examples of "transplantable tissue" include cardiovascular tissue, such as heart valves, veins, aortic grafts and the like. Additionally, the term refers to musculoskeletal tissues with which intracellular cryoprotectants are typically used, such as tendons, ligaments, cartilage and the like. Hence, allograft transplant tissue is cardiovascular or musculoskeletal tissue taken from a donor of the same species as the recipient. The preferred tissues for use herein includes veins, heart valves and musculoskeletal tissues and the most preferred tissues are heart valves, and in particular allograft heart valves.

"Elution" and "dilution" refer to the solution and process used which causes the intracellular cryoprotectant to diffuse out of the cells.

The term "intracellular cryoprotectant" refers to compounds which penetrate the cells of tissue and which increase the survival of the cells when subjected to a cryopreservation and thawing procedure, resulting in minimized intracellular or cell membrane damage. Examples include dimethylsulfoxide ("DMSO"), various diols and triols, such as ethylene glycol, propylene glycol, butanediol and triol and glycerol, as well as various amides, such as formamide and acetamide. These compounds typically enter the cell by diffusing through the cell membrane and reach equilibrium in a relatively short time period. This diffusion into the cells can take from about 10 minutes to about 2 hours, after which the transplant tissue is subjected to an appropriate freezing protocol.

The transplant tissue is subject to physical as well as biochemical stress during harvesting, cryopreservation, thawing and transplant preparation. For example, tissue which is to be stored and later used for transplantation is preferably harvested from the donor within about twenty-four hours of death. The harvested tissue is stored on ice for a relatively short time period e.g., about 24 hours. It may be subjected to certain treatments and physical characterizations, e.g., antibiotic exposure, sizing, etc., and then cryopreserved using one or more intracellular cryoprotectants with or without an extracellular cryoprotectant present in the liquid cryopreservation medium. Thus, physiological and biochemical stress occur during processing, each of which can reduce the viability of the cells upon transplant.

The term "non-toxic" is used herein in the relative sense to indicate levels of cryoprotectant which are low enough to substantially avoid chemical toxicity at physiological temperatures and avoid or minimize osmotic cell lysis upon exposure of the tissue to physiological solute concentrations, such as upon exposure to blood.

The one-step method can be performed using a balanced salt solution, such as Ringers solution, or another salt solution which is essentially isoosmotic or hyperosmotic to normal tissue/cells.

Once cryopreservation and thawing are complete, the intracellular cryoprotectant is typically present at a concentration of about 1 to 2 Molar. This concentration can vary depending upon the initial concentration and upon the treatment time.

The terms "step-wise" and "multi-step" refer to the technique of changing the concentration of intracellular cryoprotectant using gradually decreasing solute concentrations in the diluent in an effort to minimize potentially lethal osmotic changes in water diffusion across the cell membrane. During the freezing and thawing processes, cryopreserved cells undergo changes in intra- and extracellular solute concentrations as a result of changes in the amount of liquid water present. Additionally, water diffuses across the cell membrane more rapidly than cryoprotectants. Since thawed tissue typically contains cryoprotectant at a concentration which is about the same as the initial treatment level, a stepwise dilution protocol has been used to minimize the potentially lethal osmotic effect of water diffusion during and after the thawing process. Therefore, partially changing the diluent medium several times during the dilution process has been thought to assist the cells in achieving normal tonicity. For example, tissue cryopreserved in 1M DMSO solution (100 ml) would be diluted by removing a portion of the DMSO containing solution and replacing it with an equal portion of diluent, and repeating this procedure after a period of equilibration, e.g. 1 minute.

The one-step elution procedure described herein reduces the factors which must be controlled during the elution process. The primary factor which is controlled is the elution time. The minimum elution time is approximately 5 minutes. This time period seems to be more than adequate to allow sufficient intracellular cryoprotectant to diffuse out of the tissue, thus achieving a substantially non-toxic intracellular concentration prior to transplant.

By selecting the proper eluent in accordance with the teachings herein, the elution time can be extended such that no end point titration is required. Hence, the transplantable tissue can be thawed and placed into the eluent prior to or during surgery, and simply retained in the solution until the surgical site is prepared to receive the transplant. The transplant tissue need not be held in the solution for a precise period of time beyond about 5 minutes. In contrast, with the multi-step procedure, the timing of the intermediate dilution steps must be precisely controlled.

To further enhance the dilution process without causing a cell-damaging net infusion of water, a substantially impermeant solute can be included. As used herein, the term "impermeant solute" refers to components which do not passively diffuse into or out of cells, and which are not actively transported across cell membranes to any great extent within the time frame of the dilution procedure. The term "impermeant" is used in the relative sense since the cell non-penetrating components used which may assist in achieving hyperosmolarity may still enter the cells to a limited degree. Examples of substantially impermeant solutes as used herein include mannitol, sorbitol, glucose (or dextrose) and sucrose. Such impermeant solutes are selected based upon the type of transplant tissue being treated, the desired osmotic pressure which can be created with a non-toxic concentration of the solute and the overall compatibility of the impermeant solute with the other components in the diluent.

The overall compatibility of the impermeant solute with the diluent and other components is important from a formulation prespective, since any reaction between components in the diluent may adversely affect the osmotic pressure and therefore reduce the effectiveness of the diluent in countering the osmotic toxic effect of the intracellular cryoprotectant.

It has been discovered that the one-step procedure described herein can be conducted with an isoosmotic or substantially hyperosmotic diluent, with or without a substantially impermeant solute, over a time period greater than about 5 minutes, which is an effective time period for reducing the intracellular cryoprotectant concentration to a substantially non-toxic level. The intracellular concentration of cryoprotectants is reduced to acceptable levels without causing a substantial degree of toxicity and without reducing cell viability to unacceptable levels.

The preferred one step diluent in this regard has a solute concentration which provides an osmotic pressure of about 400 to about 800 mOsm. The one step procedure surprisingly provides acceptable tissue viability post-transplant as compared to the tissue viability which is observed with step-wise dilution procedures.

The most preferred one-step eluent used herein provides an osmotic pressure of about 525 mOsm. The preferred eluent in this regard is lactated Ringers solution containing 5% dextrose (w/v).

When hyperosmoticity is desired, it is preferred to utilize a substantially impermeant solute in the eluent to increase the osmotic pressure without adversely affecting the intracellular electrolyte levels which may otherwise be affected.

The preferred eluent in this regard is lactated Ringers with five percent dextrose. This formulation, can be used in the one-step dilution process over at least about a five to ten minute period to reduce a pre-dilution DMSO tissue concentration of about 10%(v/v) to a pre-transplant DMSO tissue concentration of about 5%(v/v) or lower.

When glycerol has been used as the intracellular cryoprotectant, lactated Ringers with 5% dextrose is again the preferred diluent. Post-thawed tissue cryopreserved with about a 2M intracellular glycerol concentration is eluted with lactated Ringers and 5% dextrose over about a five to ten minute period, which reduces the intracellular glycerol concentration to about 0.5 to 1M or less.

An alternative preferred diluent which is useful herein contains Dulbecco's Modified Eagles Medium ("DMEM") with or without a substantially impermeant solute.

The preferred substantially impermeant solutes useful with DMEM is 0.5M mannitol.

The effectiveness of the one-step process relative to the multistep procedure in maintaining cellular viability and functional integrity can be demonstrated by evaluating the tissue before and after a cryopreservation-thaw-dilution cycle has been performed. The one-step eluted tissue can be compared to tissue which has been cryopreserved, thawed, and then diluted using the multi-step process.

EXAMPLE 1

Human heart valve leaflets are bisected to provide a control tissue and a comparison sample. The segments are cryopreserved in DMEM with 10% fetal calf serum and 10% DMSO. The segments are then thawed and eluted with the eluent solution as described below.

The three-step (Control) dilution process is conducted as follows. Prior to elution, segments are thawed at 37° C. to 42° C. in 1 ml of the cryopreservation fluid described above. The contents, including the segments and fluid, are transfered into snap-cap tubes. The eluting solution is DMEM, low glucose with glutamine and Hepes. Eluting solution (0.35 mls) is added to the segment and its DMSO containing solution. The tube is agitated gently for one minute.

A further 0.65 mls of the eluting solution is added and the contents are agitated gently for an additional one minute.

Next, one ml of the solution is removed from the tube and discarded, and 1 ml of the eluting solution is added to the tube with gentle agitation for one minute.

After the one minute period, the leaflet segment is removed from the tube and placed into 1 ml of the eluting solution.

After one minute in the eluting solution the leaflet segment is ready for the viability assay.

The one-step elution process is performed using DMEM as the eluent over a period of 5 minutes. Cryopreserved and thawed leaflet segments are removed from the cryoprotectant solution and placed directly into DMEM. After 5 minutes, the segments are ready for the viability assay.

To conduct the viability assay, eluted tissue segments are placed in snap cap tubes (FALCON) containing 12 micro-Curie ($\mu$Ci) tritiated glycine in 750 microliter of DMEM supplemented with 15 micrograms/milliliter ascorbic acid. Radiolabeled glycine incorporation is determined after 48 hours incubation at 37° C. in an atmosphere containing 5% $CO_2$ in air.

The leaflets are then washed four times with phosphate-buffered saline solution, dehydrated with ethanol and ether, air dried and weighed.

The leaflets are rehydrated with 200microliters of water and solubilized by addition of 1M NaOH. The leaflets are then incubated at 60° C. for 1 hour and subjected to 2 twenty second sonications.

The resulting homogenates are centrifuged at 12,000×g and 100 microliters aliquots of the supernatants are placed on glass fiber filter discs (WHATMAN No. 1822024, Whatman Chemical Separation, Inc. Clifton, N.J.). The filter discs are dried and the proteins precipitated by addition of ice-cold 10% trichloroacetic acid for 30 minutes, followed by five ethanol rinses, two ether rinses and drying. The discs are then placed in 1 ml of PROTOSOL (DuPont), a protein solubilizing agent, followed by 10 ml of scintillation fluid (ECOSCINT A; National Diagnostics, Inc., Somerville, N.J.). Tritium incorporation is then measured (Beckman Instruments, Inc., Palo Alto, Calif.). The results, which are expressed in disintegrations per minute (DPM) per mg. tissue dry weight, are set forth in Table I below.

TABLE I

| VALVE | CONTROL (3-STEP) | DMEM (1-STEP) | % |
|---|---|---|---|
| (a) | 2671 | 2277 | 85% |
| (b) | 7711 | 4894 | 63% |
| (c) | 1842 | 1799 | 98% |
| (d) | 3444 | 2559 | 74% |
| (e) | 1064 | 915 | 86% |
| (f) | 2229 | 1928 | 86% |
| (g) | 1155 | 1232 | 107% |
| (h) | 2450 | 2625 | 107% |
| (i) | 1456 | 1694 | 116% |
| (j) | 1428 | 1728 | 121% |
| (k) | 2591 | 3759 | 139% |
| (l) | 2632 | 2576 | 98% |
| (m) | 2663 | 1974 | 74% |
| (n) | 1960 | 1561 | 80% |
| (o) | 1299 | 1392 | 107% |
| (p) | 1668 | 1657 | 99% |
| (q) | 2659 | 2945 | 111% |

TABLE I-continued

| VALVE | CONTROL (3-STEP) | DMEM (1-STEP) | % |
|---|---|---|---|
| AVG | 2407 | 2206 | 97% |
| | | x ± SE = 97 ± 5 | |

EXAMPLE 2

The procedure described above with respect to the one-step elution process in Example 1 was repeated except that lactated Ringers solution was substituted for DMEM in the elution step. The results are shown below in Table II.

TABLE II

| VALVE | CONTROL (3-STEP) | LR (1-STEP) | % |
|---|---|---|---|
| (a) | 2030 | 1369 | 67% |
| (b) | 5029 | 2978 | 59% |
| (c) | 3279 | 2092 | 64% |
| (d) | 4369 | 4592 | 105% |
| (e) | 2298 | 1386 | 60% |
| (f) | 3460 | 2580 | 75% |
| (g) | 1925 | 1645 | 85% |
| (h) | 2849 | 2520 | 88% |
| (i) | 1505 | 1253 | 83% |
| (j) | 1338 | 1757 | 131% |
| (k) | 2669 | 2587 | 97% |
| (l) | 2897 | 3315 | 114% |
| (m) | 2328 | 2867 | 123% |
| (n) | 1823 | 1816 | 100% |
| (o) | 3711 | 1611 | 43% |
| (p) | 1464 | 1419 | 97% |
| (q) | 5876 | 4885 | 83% |
| AVG | 2873 | 2392 | 87% |
| | | x ± SE = 87 ± 6 | |

EXAMPLE 3

The procedure described above with respect to the one-step elution process in Example 1 was repeated except that the eluent was replaced with DMEM with 0.5M mannitol. The results are shown below in Table III.

TABLE III

| VALUE | CONTROL (3-STEP) | DMEM W/ MANNITOL (1-STEP) | % |
|---|---|---|---|
| (a) | 2103 | 3081 | 146% |
| (b) | 3360 | 2622 | 78% |
| (c) | 2326 | 3733 | 160% |
| (d) | 5704 | 5450 | 96% |
| (e) | 1486 | 1658 | 112% |
| (f) | 2643 | 1195 | 45% |
| (g) | 1715 | 1925 | 112% |
| (h) | 2226 | 2898 | 130% |
| (i) | 1414 | 2072 | 147% |
| (j) | 1326 | 1620 | 122% |
| (k) | 2398 | 3608 | 150% |
| (l) | 1451 | 2212 | 152% |
| (m) | 4538 | 2948 | 65% |
| (n) | 2419 | 2142 | 89% |
| (o) | 1631 | 1185 | 73% |
| (p) | 1388 | 1992 | 144% |
| (q) | 7434 | 5224 | 70% |
| AVG | 2680 | 2680 | 111% |
| | | x ± SE = 111 ± 9 | |

EXAMPLE 4

The one-step elution process was compared to the three step protocol using lactated Ringers solution with 5% dextrose. The one step process was used to elute cryoprotectant (10% DMSO) from cryopreserved and thawed valve leaflets with lactated Ringers solution containing 5% dextrose. (Treatment B). The DPM/mg dry weight is compared to that obtained with the three step elution process using DMEM as the eluent (Treatment A). For valves 1 to 3, each leaflet was dissected from the valve and cut in half. Each half was placed into a separate cryovial and cryopreserved in DMEM with 10% fetal calf serum and 10% DMSO. All three samples were cryopreserved and then thawed in a 45° C. water bath.

Valves 4 to 6 were cryopreserved whole, thawed as described above and then bisected. Each leaflet half was then eluted separately. The results are shown below in Table IV.

TABLE IV

| VALVE | DPM/mg dry weight | | % (B/A × 100) |
|---|---|---|---|
| | Treatment A | Treatment B | |
| 1 | 597 | 922 | 154 |
| | 1203 | 1761 | 146 |
| | 985 | 1064 | 108 |
| 2 | 255 | 337 | 132 |
| | 262 | 274 | 105 |
| | 300 | 399 | 133 |
| 3 | 3003 | 2574 | 86 |
| | 2784 | 3047 | 109 |
| | 3630 | 2571 | 71 |
| | | | x ± SE = 116 ± 9 |
| 4 | 1034 | 1080 | 104 |
| | 1609 | 1060 | 66 |
| | 1152 | 908 | 79 |
| 5 | 1169 | 1232 | 105 |
| | 1397 | 1449 | 104 |
| | 1144 | 1412 | 123 |
| 6 | 1880 | 1481 | 79 |
| | 2493 | 3147 | 126 |
| | 2115 | 3052 | 144 |
| | | | x ± SE = 103 ± 8 |

While certain preferred embodiments of the invention have been described herein in detail, numerous alternative embodiments will be apparent from the teachings herein. Consequently the scope of the claims is not to be limited thereby.

We claim:

1. In a process for treating a transplantable tissue which has been cryopreserved with an intracellular cryoprotectant and thawed prior to transplantation, the improvement comprising eluting the intracellular cryoprotectant to a substantially non-toxic concentration with a solution in only a single step prior to transplantation.

2. The process of claim 1 wherein the solution is comprised of a balanced salt solution.

3. The process of claim 2 wherein the solution is comprised of lactated Ringers solution.

4. The process of claim 1, 2 or 3 wherein the solution is hyperosmotic.

5. The process of claim 2 wherein the solution is further comprised of a substantially impermeant solute.

6. The process of claim 5 wherein the substantially impermeant solute is comprised of dextrose.

7. The process of claim 3 wherein the cryoprotected transplantable tissue has a final cryoprotectant concentration of about 0.25M to about 1M.

8. The process of claim 7 wherein the intracellular cryoprotectant is dimethylsulfoxide.

9. The process of claim 3 wherein the transplantable tissue is immersed in the solution at a temperature of about 0° C. to about 38° C.

10. The process of claim 1 wherein the transplantable tissue is cardiovascular or musculoskeletal tissue.

11. The process of claim 10 wherein the transplantable tissue is a vein, artery, heart valve, ligament or tendon.

12. The process of claim 11 wherein the transplantable tissue is a heart valve.

13. The process of claim 12 wherein the heart valve is an allograft heart valve.

14. A process for reducing the concentration of intracellular cryoprotectant in a cryopreserved and thawed transplantable tissue comprising:
treating the tissue with a solution after thawing to cause elution of the cryoprotectant out of the tissue in only a single step until the cryoprotectant concentration is from about 0.25M to about 1M.

15. The process of claim 14 wherein the solution is further comprised of a substantially impermeant solute.

16. The process of claim 14 wherein the solution is comprised of lactated Ringers solution.

17. The process of claim 15 wherein the substantially impermeant solute is comprised of dextrose.

18. In a process for treating a transplantable tissue prior to transplantation which has been cryopreserved with an intracellular cryoprotectant and thawed, the improvement comprising diluting the intracellular cryoprotectant with a solution comprised of lactated Ringers solution and 5% dextrose in only a single elution step prior to transplantation without substantially reducing the viability of the transplantable tissue upon transplantation into a patient in need of such treatment.

19. The process of claim 18 wherein the transplantable tissue is cardiovascular or musculosketal tissue.

20. The process of claim 19 wherein the transplantable tissue is a vein, artery, heart valve, ligament or tendon.

21. The process of claim 20 wherein the transplantable tissue is a heart valve.

22. The process of claim 21 wherein the heart valve is an allograft heart valve.

* * * * *